United States Patent
Chatterjee et al.

(10) Patent No.: US 11,371,978 B1
(45) Date of Patent: Jun. 28, 2022

(54) SYSTEM AND METHOD FOR DETECTING LEAD IN WATER

(71) Applicants: Somak Chatterjee, Pilani (IN); Krishna Etika, Pilani (IN); Andrew Krause, Louisville, KY (US); Dustan Lee Hahn, Tampa, FL (US); Harkirat Sahni, Tampa, FL (US)

(72) Inventors: Somak Chatterjee, Pilani (IN); Krishna Etika, Pilani (IN); Andrew Krause, Louisville, KY (US); Dustan Lee Hahn, Tampa, FL (US); Harkirat Sahni, Tampa, FL (US)

(73) Assignee: MKS VISION, LLC, Louisville, KY (US)

( * ) Notice: Subject to any disclaimer, the term of this patent is extended or adjusted under 35 U.S.C. 154(b) by 0 days.

(21) Appl. No.: 17/356,313

(22) Filed: Jun. 23, 2021

(51) Int. Cl.
  *G01N 33/18* (2006.01)
  *G01N 27/07* (2006.01)
  (Continued)

(52) U.S. Cl.
  CPC ....... *G01N 33/1813* (2013.01); *C01B 32/158* (2017.08); *G01N 27/07* (2013.01);
  (Continued)

(58) Field of Classification Search
  CPC .. G01N 33/1813; G01N 27/07; G01N 27/127; B82Y 30/00; B82Y 35/00;
  (Continued)

(56) References Cited

U.S. PATENT DOCUMENTS

| 6,810,732 B2 | 11/2004 | Shon |
| 7,651,858 B2 | 1/2010 | Bakker et al. |

(Continued)

FOREIGN PATENT DOCUMENTS

| CA | 2822876 | 6/2012 |
| CA | 3006221 | 6/2017 |

(Continued)

OTHER PUBLICATIONS

He, Xiuhui, et al. "Square wave anodic stripping voltammetric determination of lead (II) using a glassy carbon electrode modified with a lead ionophore and multiwalled carbon nanotubes." Microchimica Acta 176.1 (2012): 81-89. (Year: 2012).*

(Continued)

*Primary Examiner* — Robert J Eom
(74) *Attorney, Agent, or Firm* — Steve LeBlanc, LLC

(57) ABSTRACT

A system for measuring a concentration of lead in water includes a variable electrode having a mixture of lead ionophore II, carbon nanotubes, and a first binder. A reference electrode includes a mixture of carbon nanotubes and a second binder. A meter is electrically connected in series with the variable and reference electrodes, and the meter generates a signal reflective of the concentration of lead in the water when the variable and reference electrodes are immersed in the water. A method for measuring a concentration of lead in water may include preparing a variable electrode having lead ionophore II and a reference electrode having carbon nanotubes. The method may further include electrically connecting a meter with the variable and reference electrodes, immersing the variable and reference electrodes in the water, and generating a signal from the meter reflective of the concentration of lead in the water.

17 Claims, 2 Drawing Sheets

(51) Int. Cl.
*G01N 27/12* (2006.01)
*C01B 32/158* (2017.01)
*B82Y 30/00* (2011.01)
*B82Y 40/00* (2011.01)
*B82Y 35/00* (2011.01)

(52) U.S. Cl.
CPC ............ *G01N 27/127* (2013.01); *B82Y 30/00* (2013.01); *B82Y 35/00* (2013.01); *B82Y 40/00* (2013.01); *C01B 2202/22* (2013.01); *C01P 2004/13* (2013.01); *C01P 2004/64* (2013.01); *C01P 2006/40* (2013.01)

(58) Field of Classification Search
CPC ... B82Y 40/00; C01B 32/158; C01B 2202/22; C01P 2004/13; C01P 2004/64; C01P 2006/40
See application file for complete search history.

(56) References Cited

U.S. PATENT DOCUMENTS

| | | | |
|---|---|---|---|
| 7,866,204 | B2 | 1/2011 | Yang et al. |
| 8,920,619 | B2 | 12/2014 | Salzer et al. |
| 9,719,975 | B1 | 8/2017 | Basheer et al. |
| 10,955,400 | B2 | 3/2021 | Lin et al. |
| 2007/0199816 | A1 | 8/2007 | Sun et al. |
| 2008/0283395 | A1 | 11/2008 | Rhee et al. |
| 2013/0059391 | A1 | 3/2013 | Zhang et al. |
| 2015/0137189 | A1 | 5/2015 | Pace et al. |
| 2016/0231271 | A1* | 8/2016 | Huang ............... C08G 73/0273 |
| 2016/0356713 | A1 | 12/2016 | Chen et al. |
| 2017/0102330 | A1 | 4/2017 | Ma et al. |
| 2019/0017978 | A1* | 1/2019 | Dubus .................... C09B 19/00 |

FOREIGN PATENT DOCUMENTS

| | | |
|---|---|---|
| CN | 103305612 | 1/2015 |
| CN | 104569112 | 4/2015 |
| CN | 103278497 | 7/2015 |
| JP | 5892988 B2 | 3/2016 |
| RU | 2682162 C1 | 3/2019 |
| WO | WO 2007/053154 | 5/2007 |
| WO | WO 2010/051842 A1 | 5/2010 |
| WO | WO 2011/124945 A1 | 10/2011 |
| WO | 2013/141692 | 9/2013 |
| WO | WO 2016/141337 | 9/2016 |
| WO | 2018/217782 | 11/2018 |

OTHER PUBLICATIONS

Rius-Ruiz, F. Xavier, et al. "Disposable planar reference electrode based on carbon nanotubes and polyacrylate membrane." Analytical chemistry 83.14 (2011): 5783-5788. (Year: 2011).*

Wang, Cong, et al. "MWCNT/Nafion/Lead Ionophore Modified Electrode for the Detection of Trace Pb2+ in Coastal Seawater." Journal of Physics: Conference Series. vol. 1820. No. 1. IOP Publishing, 2021. (Year: 2021).*

Product Information, Merck KGaA, Darmstadt, Germany, 2018, p. 1-3, (https://www.sigmaaldrich.com/deepweb/assets/sigmaaldrich/product/documents/272/461/15336.pdf). (Year: 2018).*

DuPont 7102 Technical Data Sheet, DuPont, 2009, p. 1-2, (https://www.dupont.com/content/dam/dupont/amer/us/en/transportation-industrial/public/documents/en/7102.pdf). (Year: 2009).*

Xiaochao Tang, Po-Yen Wang and Gabrielle Buchter, Ion-Selective Electrodes for Detection of Lead (II) in Drinking Water: A Mini-Review, Published Aug. 24, 2018.

* cited by examiner

SYSTEM AND METHOD FOR DETECTING LEAD IN WATER

FIELD OF THE INVENTION

The present invention generally involves a system and method for detecting and/or measuring a concentration of lead in water. In particular embodiments, the system and method may be incorporated into a water supply or an appliance to detect and/or measure the amount of lead present in the water.

BACKGROUND OF THE INVENTION

Heavy metals such as lead create adverse health effects even in trace quantities. Lead-based plumbing is a common source of lead contamination in drinking water, and despite widespread studies and efforts to detect and eliminate such contamination, lead contamination in drinking water continues to occur.

Current systems and methods to detect the presence of lead in water rely on various combinations of large and/or expensive equipment, skilled operators, and/or slow response times. For example, atomic absorption spectroscopy can rapidly detect and measure the concentration of lead in water, but the equipment costs tens of thousands of dollars and requires skilled operators to use. Lead ion selective electrodes provide a less expensive alternative; however, they have a slower response time and still require operator action and calibration to obtain and analyze samples. Therefore, the need exists for a cost-effective system and method to detect and/or measure the concentration of lead in water.

BRIEF DESCRIPTION OF THE INVENTION

Aspects and advantages of the invention are set forth below in the following description, or may be obvious from the description, or may be learned through practice of the invention.

One embodiment of the present invention is a system for measuring a concentration of lead in water that includes a variable electrode having a mixture of lead ionophore II, carbon nanotubes, and a first binder. A reference electrode includes a mixture of carbon nanotubes and a second binder. A meter is electrically connected in series with the variable electrode and the reference electrode, and the meter generates a signal reflective of the concentration of lead in the water when the variable electrode and the reference electrode are immersed in the water.

An alternate embodiment of the present invention is a system for measuring a concentration of lead in water that includes a variable electrode having lead ionophore II and a reference electrode electrically connected to the variable electrode and having carbon nanotubes. A meter is electrically connected with the variable electrode and the reference electrode, and the meter generates a signal reflective of the concentration of lead in the water when the variable electrode and the reference electrode are immersed in the water.

In yet another embodiment of the present invention, a method for measuring a concentration of lead in water may include the steps of preparing a variable electrode having lead ionophore II and a reference electrode having carbon nanotubes. The method may further include electrically connecting a meter with the variable and reference electrodes, immersing the variable and reference electrodes in the water, and generating a signal from the meter reflective of the concentration of lead in the water.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
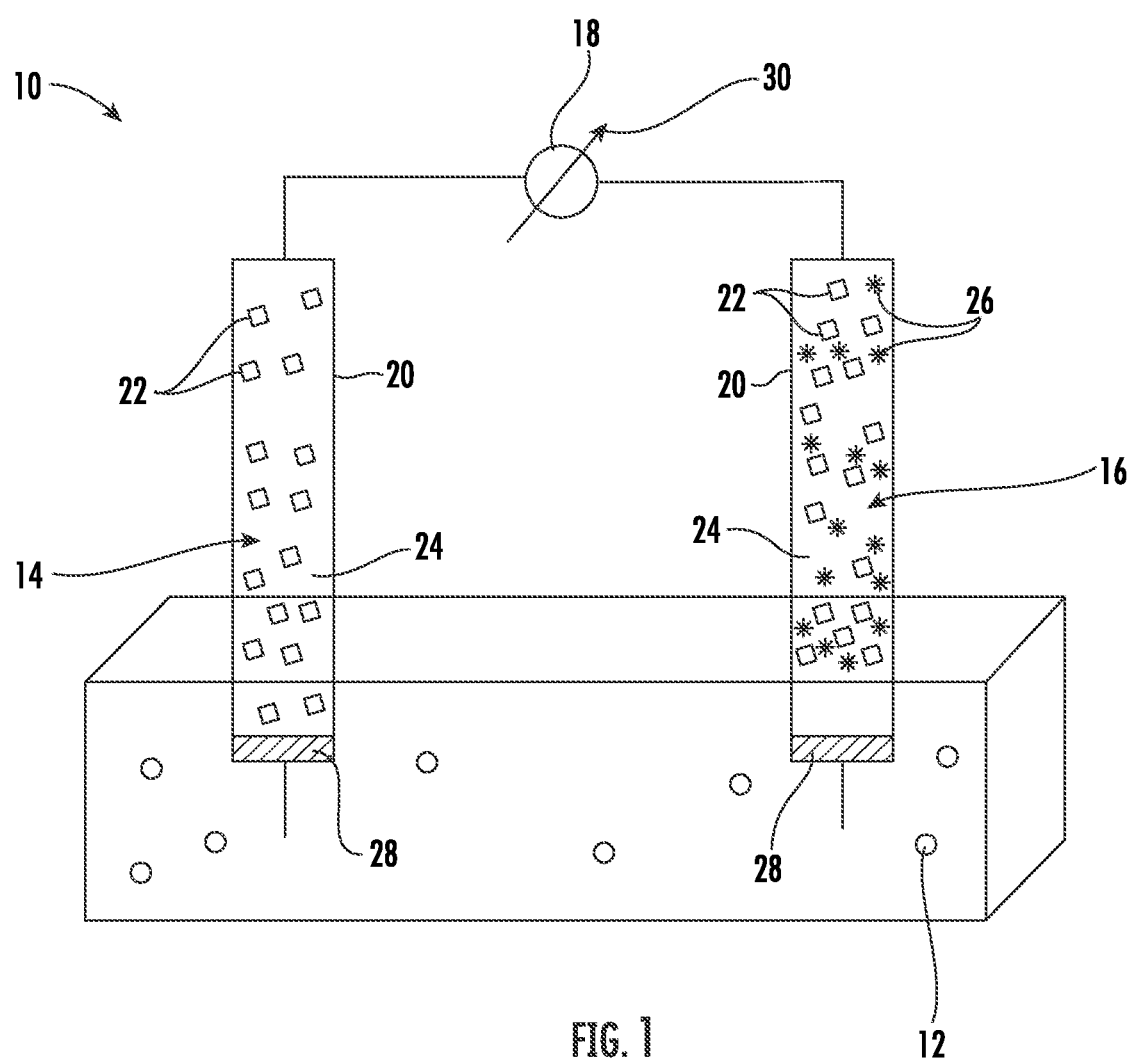
FIG. 1 is a schematic drawing of a system for measuring a concentration of lead in water.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

As used in the claims, the definite article "said" identifies required elements that define the scope of embodiments of the claimed invention, whereas the definite article "the" merely identifies environmental elements that provide context for embodiments of the claimed invention that are not intended to be a limitation of any claim. As used herein, the term "fluid communication" refers to a fluid pathway, and components are in fluid communication with each other if a fluid pathway exists between the components. As used herein, the terms "upstream" and "downstream" refer to the location of items with reference to the direction of fluid flow in a fluid pathway. For example, item A is "upstream" from item B and item B is downstream from item A if fluid normally flows from item A to item B.

Embodiments of the present invention include a system and method for detecting and/or measuring a concentration of lead in water. The system and method may be operated as a standalone device or integrated into or incorporated upstream or downstream from an appliance to detect the presence of lead in a water supply. In particular embodiments, the system and method may be used to monitor batch samples or continuous streams of water without requiring any operator actions.

FIG. 1 provides a schematic drawing of a system 10 for measuring a concentration of lead 12 in water. As shown in FIG. 1, the system 10 generally includes an electrical circuit with a reference electrode 14 and a variable electrode 16 immersed in the water to be tested. The distance between the reference and variable electrodes 14, 16 affects the sensitivity of the system 10, and a suitable distance to detect lead concentrations as low as 1 ppb may be approximately 3 centimeters. A meter 18 electrically connected with the electrodes 14, 16 measures the electrical potential between the electrodes 14, 16 created by the presence of lead 12 in the water.

The reference electrode 14 is designed to maintain a consistent conductivity regardless of the lead 12 concentration in the water. In general, the reference electrode 14 includes a mixture of highly conductive material in a glass or plastic tube or other non-conductive container 20. For example, the reference electrode 14 may include carbon nanotubes 22 mixed with a binder 24 to create a paste-like substance. The binder 24 may be silicon oil, polyvinyl alcohol, or another water soluble polymer with an affinity for carbon nanotubes 20. Increasing the ratio of carbon nanotubes 22 to binder 24 material increases the conductivity of the reference electrode 14. In particular embodiments, the concentration of carbon nanotubes 22 in the reference electrode 14 may be 70-80% by weight.

The variable electrode 16 is designed to vary conductivity based on the lead 12 concentration in the water. As with the reference electrode 14, the variable electrode 16 also includes a mixture of highly conductive material, such as carbon nanotubes 22 and binder 24, in a glass or plastic tube or other non-conductive container 20. In addition, the variable electrode 16 includes lead ionophore II ($C_{19}H_{38}N_2S_4$) 26 which reacts with lead 12 in the water to transfer ions from the water into the variable electrode 16. In particular embodiments, the concentration of lead ionophore II 26 in the variable electrode 16 may be 20-30% by weight, and the concentration of carbon nanotubes 22 in the variable electrode 16 may be 50-60% by weight.

The mixtures of carbon nanotubes 22 and binder 24 in the reference electrode 14 and carbon nanotubes 22, binder 24, and lead ionophore II 26 in the variable electrode 16 may be in direct contact with the water being sampled. Alternately, as shown in FIG. 1, the system 10 may further include a hydrophilic membrane 28 between either or both of the reference and variable electrodes 14, 16 and the water. The hydrophilic membrane 28 may be polyvinyl alcohol or any hydrophilic polymer that is generally permeable to water and lead ions and impermeable to other ions that might interfere with the sensitivity and/or accuracy of the system 10. In this manner, the hydrophilic membrane 28 retains the mixtures in the respective electrodes 14, 16 while selectively allowing the lead ionophore II 26 to transfer ions from lead 12 in the water to the variable electrode 16 to increase the electrical potential between the reference and variable electrodes 14, 16.

The meter 18 may be electrically connected in series or parallel to the electrodes 14, 16, depending on the particular desired measurement. The meter 18 may be a potentiometer, voltmeter, or other instrument suitable for measuring the electrical potential between the reference and variable electrodes 14, 16 created by the presence of lead 12 in the water. Specifically, the lead ionophore II 26 in the variable electrode 16 binds with lead ions in the water and transfers the lead ions through the hydrophilic membrane 28, if present, to the variable electrode 16. The amount of lead ions transferred to the variable electrode 16 is proportional to the concentration of lead 12 in the water and produces a corresponding proportional electrical potential between the reference and variable electrodes 14, 16 that may be measured by the meter 18. In this manner, the meter 18 generates a signal 30 reflective of the concentration of lead 12 in the water when the reference and variable electrodes 14, 16 are immersed in the water, as shown in the following exemplary table.

| Lead Concentration (ppm) | Signal (mV) |
|---|---|
| 1000 | 138 ± 10 |
| 100 | 76 ± 10 |
| 10 | 40 ± 10 |
| 1 | 20 ± 10 |

Figure 2:
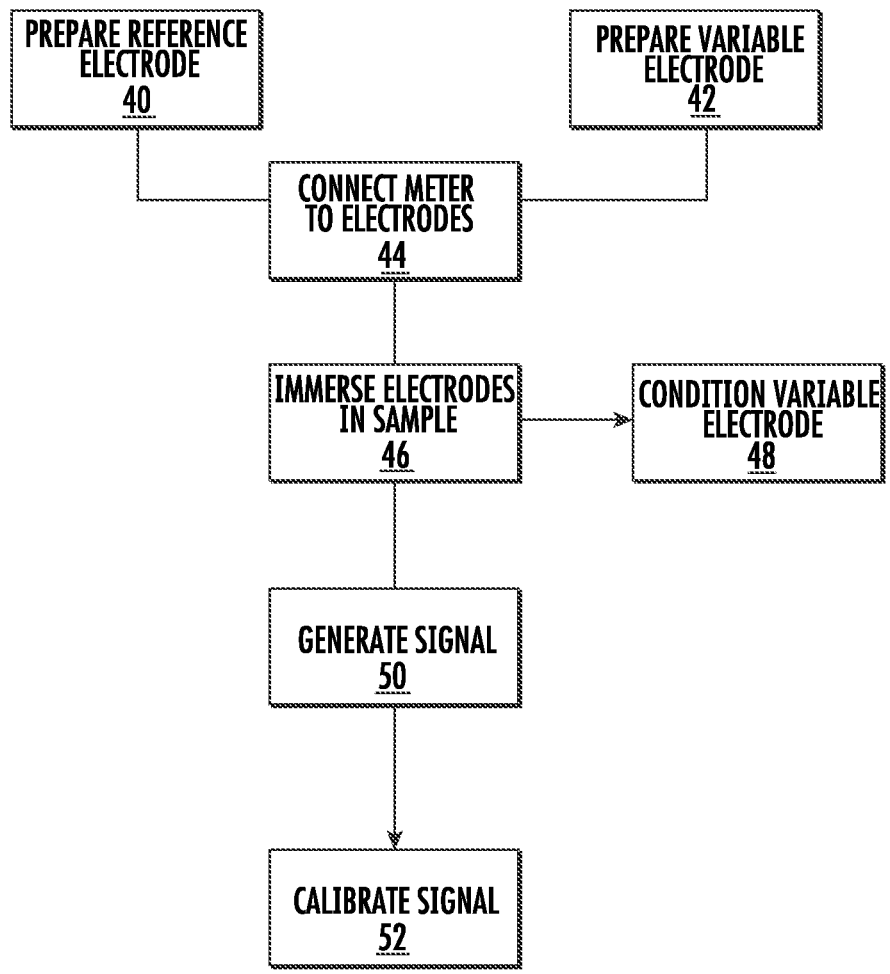
FIG. 2 is a flow diagram of a method for measuring a concentration of lead in water.

FIG. 2 provides a flow diagram of a method for measuring a concentration of lead in water using the system 10 described and illustrated in FIG. 1. Block 40 represents the step of preparing the reference electrode 14 with carbon nanotubes 22. In particular embodiments, the method may include mixing 70-80% by weight of carbon nanotubes 22 with the binder 24 in the reference electrode 14. Block 42 represents the step of preparing the variable electrode 16 with lead ionophore II 26. In particular embodiments, the method may include mixing 20-30% by weight of lead ionophore II 26 with 50-60% by weight of carbon nanotubes 22 in the variable electrode 16. In addition, other particular embodiments may include the step of separating the reference and/or variable electrodes 14, 16 from the water with the hydrophilic membrane 28.

Block 44 represents the step of electrically connecting the meter 18 in series with the reference and variable electrodes 14, 16. Block 46 represents the step of immersing the reference and variable electrodes 14, 16 in the water to be sampled. As previously discussed, the water to be sampled may be a batch sample or a continuous flow of water by the immersed reference and variable electrodes 14, 16.

Block 48 represents the step of conditioning the variable electrode 16 by immersing the variable electrode 16 in a lead 12 solution for at least five minutes. The optimum concentration of lead 12 in solution and duration of the conditioning may vary according to several operational and/or design parameters, such as the desired sensitivity of the system 10 to lead 12, the particular composition of the lead ionophore II 26 and carbon nanotubes 22 in the variable electrode 16, and the presence and/or thickness of the hydrophilic membrane 28.

Block 50 represents the step of generating the signal 30 from the meter 18 reflective of the concentration of lead 12 in the water. As previously described, the lead ionophore II 26 in the variable electrode 16 interacts with lead 12 in the water and transfers ions into the variable electrode 16 corresponding to the concentration of lead 12 in the water. The additional ions transferred into the variable electrode 16 produces a corresponding change in electrical potential between the reference and variable electrodes 14, 16. As a result, the signal 30 generated by the meter 18 reflects the concentration of lead 12 in the water.

Block 52 represents the step of calibrating the signal 30 generated from the meter 18 with known concentrations of lead 12 so that the signal 30 will more accurately reflect the concentration of lead 12 in the water during use. Specifically, the magnitude of the electrical potential between the reference and variable electrodes 14, 16 for a given concentration of lead 12 in the water will vary according to several variables associated with the system 10 and the water being sampled. For example, a greater distance between the electrodes 14, 16 generally reduces the electrical potential between the reference and variable electrodes 14, 16 for a given concentration of lead 12 in the water. Similarly, the concentration of lead ionophore II 26 and carbon nanotubes 22 in the reference and variable electrodes 14, 16 may vary between systems and directly impacts the electrical potential between the reference and variable electrodes 14, 16 for a given concentration of lead 12 in the water. Lastly, several characteristics of the water being sampled, such as the temperature, pH, and concentration of interfering ions, may increase or decrease the electrical potential between the reference and variable electrodes 14, 16 for a given concentration of lead 12 in the water. Calibrating the signal 30 generated from the meter 18 with known concentrations of lead 12 thus adjusts the magnitude and changes in magnitude of the signal 30 to more closely correspond to the concentration and changes in concentration of lead 12 in the water.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A system for measuring a concentration of lead in water, comprising:
    a variable electrode comprising a mixture of lead ionophore II, carbon nanotubes, and a first binder;
    a reference electrode comprising a mixture of carbon nanotubes and a second binder;
    a hydrophilic membrane between said variable electrode and the water;
    a meter electrically connected in series with said variable electrode and said reference electrode; and
    wherein said meter generates a signal reflective of the concentration of lead in the water when said variable electrode and said reference electrode are immersed in the water.

2. The system for measuring the concentration of lead in water as in claim 1, wherein said variable electrode has a concentration of lead ionophore II of 20-30% by weight.

3. The system for measuring the concentration of lead in water as in claim 1, wherein said variable electrode has a concentration of carbon nanotubes of 50-60% by weight.

4. The system for measuring the concentration of lead in water as in claim 1, wherein said reference electrode has a concentration of carbon nanotubes of 70-80% by weight.

5. The system for measuring the concentration of lead in water as in claim 1, wherein said first and second binders are selected from the group consisting of silicon oil or polyvinyl alcohol.

6. A system for measuring a concentration of lead in water, comprising:
    a variable electrode comprising lead ionophore II;
    a reference electrode electrically connected to said variable electrode and comprising carbon nanotubes;
    a hydrophilic membrane between said variable electrode and the water;
    a meter electrically connected with said variable electrode and said reference electrode; and
    wherein said meter generates a signal reflective of the concentration of lead in the water when said variable electrode and said reference electrode are immersed in the water.

7. The system for measuring the concentration of lead in water as in claim 6, wherein said variable electrode has a concentration of lead ionophore II of 20-30% by weight.

8. The system for measuring the concentration of lead in water as in claim 6, wherein said variable electrode further comprises 50-60% by weight of carbon nanotubes.

9. The system for measuring the concentration of lead in water as in claim 6, wherein said variable electrode further comprises a binder selected from the group consisting of silicon oil or polyvinyl alcohol.

10. The system for measuring the concentration of lead in water as in claim 6, wherein said reference electrode has a concentration of carbon nanotubes of 70-80% by weight.

11. A method for measuring a concentration of lead in water, comprising:
    preparing a variable electrode comprising lead ionophore II;
    preparing a reference electrode comprising carbon nanotubes;
    separating said variable electrode from the water with a hydrophilic membrane;
    electrically connecting a meter with said variable electrode and said reference electrode;
    immersing said variable electrode and said reference electrode in the water; and
    generating a signal from said meter reflective of the concentration of lead in the water.

12. The method for measuring the concentration of lead in water as in claim 11, further comprising mixing 20-30% by weight of lead ionophore II in said variable electrode.

13. The method for measuring the concentration of lead in water as in claim 11, further comprising mixing 50-60% by weight of carbon nanotubes in said variable electrode.

14. The method for measuring the concentration of lead in water as in claim 11, further comprising mixing 70-80% by weight of carbon nanotubes in said reference electrode.

15. The method for measuring the concentration of lead in water as in claim 11, further comprising mixing a binder selected from the group consisting of silicon oil or polyvinyl alcohol in said variable electrode.

16. The method for measuring the concentration of lead in water as in claim 11, further comprising conditioning said variable electrode by immersing said variable electrode in a lead solution for at least five minutes.

17. The method for measuring the concentration of lead in water as in claim 11, further comprising calibrating said signal generated from said meter with known concentrations of lead.

* * * * *